US007423186B2

(12) United States Patent
Standke et al.

(10) Patent No.: US 7,423,186 B2
(45) Date of Patent: Sep. 9, 2008

(54) PROCESS FOR PREPARING ALKOXY-PURE ALKALINE EARTH ALKOXIDES

(75) Inventors: Burkhard Standke, Lörrach (DE); Hartwig Rauleder, Rheinfelden (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 11/010,831

(22) Filed: Dec. 13, 2004

(65) Prior Publication Data
US 2005/0131257 A1 Jun. 16, 2005

(30) Foreign Application Priority Data
Dec. 13, 2003 (DE) ................. 103 58 411

(51) Int. Cl.
*C07C 41/14* (2006.01)
(52) U.S. Cl. ................. 568/679; 568/678; 568/851
(58) Field of Classification Search ................. 568/679, 568/851, 678
See application file for complete search history.

(56) References Cited

U.S. PATENT DOCUMENTS 2,965,663 A 12/1960 Smith et al.
4,327,230 A * 4/1982 Ackermann et al. ......... 568/851
4,681,959 A 7/1987 Ayen
4,728,704 A * 3/1988 Chadwick et al. ......... 526/125.2
4,876,230 A * 10/1989 Job ............................. 502/171

FOREIGN PATENT DOCUMENTS

| DE | 2 261 386 | 7/1974 |
| EP | 0 026 547 A1 | 4/1981 |
| GB | 667708 | 3/1952 |
| GB | 767601 | 2/1957 |

OTHER PUBLICATIONS

"Alkoxides, Metal," Kirk-Othmer Encyclopedia of Chemical Technology, pp. 8-9, 3$^{rd}$ ed., vol. 2 no date provided.
Meerwein, Hans et al., "Ein neues Verfahren zur Reduktion von Aldehyden und Ketonen," Liebigs Annalen der Chemie 444, Jun. 25, 1925, Chemical Department of the University of Königsberg, Germany.
Sigma-Aldrich Co.; 2 pgs., 2007 catalog (online).

* cited by examiner

*Primary Examiner*—Rosalynd Keys
(74) *Attorney, Agent, or Firm*—Robert G. Weilacher; Smith, Gambrell & Russell

(57) ABSTRACT

The present invention provides a process for preparing a metal-free alkaline earth methanolate by alcoholysis of an alkaline earth ethanolate with methanol.

1 Claim, No Drawings

PROCESS FOR PREPARING ALKOXY-PURE ALKALINE EARTH ALKOXIDES

The invention provides a process for preparing an alkaline earth dimethanolate, also called alkaline earth methanolate in the following.

Alkaline earth methanolates are used in a variety of ways in organic synthetic chemistry.

The most common process for preparing these is the direct reaction of alkaline earth metal with alcohol, with the elimination of hydrogen [Liebigs Annalen der Chemie 444, 236 (1925)]. This reaction is extraordinarily difficult when using longer chain alcohols as a result of the low affinity of the reaction partners to each other.

U.S. Pat. Ser. No. 2,965,663 discloses the reaction of metals from groups IA, IIA and IIIA of the Periodic System of Elements (PSE) with alcohols to give the corresponding alkoxides using a special reflux process. The extraordinarily long reaction times, in particular when using metals from groups IIA and IIIA, are disadvantageous.

DE-OS 22 61 386 discloses that the reaction of alkaline earth metal and alcohol can be performed more rapidly at elevated temperatures, but with the disadvantage that the reaction has to be performed under high pressure in an autoclave.

A general problem when preparing alkaline earth alkoxides from an alkaline earth metal and alcohol is the residual content of unreacted metal, which interferes with subsequent use of the product, for example when magnesium alkoxide is used as a catalyst in organic synthetic chemistry.

Another route for preparing metal alkoxides uses the technique of alcoholysis (Kirk-Othmer Encyclopedia of Chemical Technology, $3^{rd}$ ed., vol. 2, pages 8 and 9).

According to current opinion, at least some of the alkoxide groups in a metal alkoxide can be replaced by alkoxide groups from another alcohol, in particular a higher alcohol.

The disadvantage of this process is that contamination by alcohol or the alkoxide of the lower alcohol is observed to remain in the product when preparing alkoxides of group IIA of the PSE. Thus, for example, during the alcoholysis of magnesium ethanolate, i.e. magnesium diethanolate, with isopropanol to give magnesium isopropanolate, i.e. magnesium di-isopropanolate, about 15 wt. % of ethanolate, calculated as ethanol, still remains in the product. A concentration of foreign alkoxide of this order of magnitude in the product may cause problems, for example when using magnesium di-isopropanolate as a catalyst in a synthesis in organic chemistry.

The present invention is therefore based on the object of providing a process for preparing metal-free magnesium methanolate.

The object is achieved according to the invention in accordance with the features in the claims.

Surprisingly, it was found that a metal-free alkaline earth methanolate of the general formula I $$M(OMe)_2 \quad (I),$$

in which M represents an element from group IIA of the Periodic System of Elements, M preferably representing magnesium, can be prepared in a simple and also economically viable manner when a compound of the general formula II $$M(OEt)_2 \quad (II),$$

in which M represents an element from group IIA of the Periodic System of Elements, is treated with an excess of methanol, i.e. is subjected to alcoholysis.

The reaction mixture is heated, in a suitable manner, to perform the present reaction. The reaction according to the invention is preferably performed at a temperature in the range 20 to 78° C. under atmospheric pressure. The aforementioned reaction is generally completed by removing the alcohols present by distillation, a vacuum also being applied for this purpose if required:

$$M(OEt^2)_2 + xMeOH \rightarrow M(OMe^1)_2 + (x-2)HOMe + 2EtOH$$

Furthermore, when performing the present process, it should be ensured that the distillation system used provides sufficient separating power.

In the context of the present invention, metal-free alkaline earth alkoxides are understood to be those which contain less than 0.04 wt. % of alkaline earth metal, with respect to the alkaline earth alkoxide. When using the present invention, metal-free alkaline earth alkoxides of the general formula I with preferably ≦0.03 wt. % of alkaline earth metal, in particular those with ≦0.02 wt. % of alkaline earth metal, down to the limit of detection of the particular alkaline earth metal are obtained, wherein the data given each time is with respect to the alkaline earth alkoxide.

Therefore the present invention provides a process for preparing a metal-free alkaline earth methanolate of the general formula I $$M(OMe)_2 \quad (I),$$

in which M represents an element from group IIA of the Periodic System of Elements, by alcoholysis of a compound of the general formula II $$M(OEt)_2 \quad (II),$$

in which M represents an element from group IIA of the Periodic System of Elements, using excess methanol.

In the process according to the invention, the ethanol or a mixture of methanol and ethanol being produced during reaction is preferably removed from the reaction mixture by distillation.

In general, the process according to the invention is performed as follows:

First, an alkaline earth ethanolate, that is an alkaline earth diethanolate, is prepared in a manner known per se by dissolving the alkaline earth metal in ethanol, optionally with heating and optionally in the presence of a catalyst. If the excess alcohol is removed after reaction, powdered metal alkoxide can be obtained. Normally, an alkaline earth ethanolate prepared in this way contains a residual proportion of alkaline earth metal of ≧0.04 wt. %, with respect to the alkaline earth metal alkoxide. Normally the alkaline earth alkoxide is handled with the exclusion of moisture and under an atmosphere of protective gas. The alkaline earth ethanolate may be used as an alcoholic solution or in the powdered form for alcoholysis according to the invention. In a suitable manner, methanol, preferably dry methanol, under a protective gas, for example dry nitrogen or argon, is initially introduced in excess in a dry, coolable and heatable reaction vessel with a stirring device and the reactant (powdered or dispersed, partly dissolved or fully dissolved in ethanol and/or methanol) is added, wherein the reaction mixture is preferably mixed well and heated to a temperature in the range 20 to 78° C., preferably 40 to 78° C. After a reaction time of 1 to 8 hours, the alcohol or alcohol mixture may be removed from the system via the gas phase, i.e. by distillation. The desired product is generally produced in powdered form and contains, in an advantageous manner, less than 10 wt. % of ethanolate.

Metal-free alkaline earth methanolates, i.e. alkaline earth dimethanolates, are obtainable in a simple and economically viable manner, even on an industrial scale, by the process according to the invention.

The present invention is explained in more detail by the following examples, without restricting the object of the invention:

EXAMPLES

Example 1

Preparation of Magnesium Dimethanolate from Magnesium Diethanolate 500 g of methanol are added to 31 g of commercially available magnesium diethanolate powder (standard particle size, manufacturer: Degussa AG) and the mixture is heated to 40° C. The magnesium ethanolate dissolves almost completely. Then the alcoholic solvent is removed at 68° C. on a Rotavapor. A white powder is left as the residue and this contains only 2 wt. % of ethanol (after hydrolysis).

Comparison Example A

Preparation of Magnesium di-n-propanolate in an Autoclave 112 g of magnesium turnings and 3 000 g of propan-1-ol are initially introduced into a 10 l steel autoclave. Reaction is performed for a total of 5 hours at 188° C. and a pressure of 38 bar. Then n-propanol is removed by distillation at a temperature of 80° C. and a pressure of about 50 mbar. The alkoxide is then dried at 80° C. and a pressure of <1 mbar. The product still contains a proportion of metallic magnesium amounting to 0.04 wt. %.

The invention claimed is:

1. A process for preparing a metal-free magnesium methanolate of the formula I $$Mg(OMe)_2 \qquad (I),$$

comprising an alcoholysis reaction of a reaction mixture containing a compound of the formula II $$Mg(OEt)_2 \qquad (II),$$

and excess methanol to thereby produce ethanol or a mixture of methanol and ethanol and removing said ethanol or said mixture of methanol and ethanol from said reaction mixture by distillation to complete the reaction and to recover powdered magnesium methanolate.

* * * * *